US005894352A

United States Patent [19]
Morton

[11] Patent Number: 5,894,352
[45] Date of Patent: Apr. 13, 1999

[54] ABSORPTION TESTER FOR OPTICAL COMPONENTS

[75] Inventor: Richard George Morton, San Diego, Calif.

[73] Assignee: Cymer, Inc., San Diego, Calif.

[21] Appl. No.: 08/859,021

[22] Filed: May 20, 1997

[51] Int. Cl.[6] .......................... G01N 21/00; G01K 17/00
[52] U.S. Cl. ........................... 356/432; 374/32; 374/45
[58] Field of Search ................................ 374/32, 45, 161; 356/432 T, 432

[56] References Cited

U.S. PATENT DOCUMENTS

| | | | |
|---|---|---|---|
| 4,429,999 | 2/1984 | Bimberg et al. | 374/32 |
| 5,011,286 | 4/1991 | Petralli | 356/343 |
| 5,141,331 | 8/1992 | Oehler et al. | 356/432 |
| 5,316,380 | 5/1994 | Secemski | 374/32 |
| 5,634,718 | 6/1997 | Martinis et al. | 374/32 |

OTHER PUBLICATIONS

D. A. Pinnow and T. C. Rich, Development of a Calorimetric Method for Making Precision Optical Absorption Measurements, Applied Optics, vol. 12, No. 5, pp. 984–992, May 1973.

E. D. West and L. B. Schmidt, Spectral–absorptance measurements for laser calorimetry, Journal of the Optical Society of America, pp. 573–578, Feb. 1975.

T. J. Magee, N.M. Johnson, M. Lehmann, J. Peng, and J. Hannigan, Compact calorimeter for measuring laser absorption coefficients of small samples, Review of Scientific Instriments, vol. 47, No. 3, pp. 301–302, Mar. 1976.

T. I. Bryushkova, E. M. Nikitin, and A. M. Prokhorov, Measurement of low absorption coefficients of glasses by a calorimetric method, Sov. J. Quantum Electron, vol. 6, No. 11, pp. 1373–1375, Nov. 1976.

M. Hass, J. W. Davisson, H. B. Rosenstock, J. Babiskin, Measurement of very low absorption coefficients by laser calorimetry, applied Optics, vol. 14, No. 5, pp. 1128–1130, May 1975.

*Primary Examiner*—Robert Kim
*Assistant Examiner*—Zandra V. Smith
*Attorney, Agent, or Firm*—Brian D. Ogonowsky

[57] ABSTRACT

The preferred embodiment of the invention measures the temperature increase of a light-transmitting optical component to determine the optical absorption of the optical component. Accurately determining the optical absorption of light-transmitting optical components advantageously allows for the accurate and efficient selection of light-transmitting optical components for use in an optical system. In one embodiment, an optical absorption tester holds multiple optical components and, for each optical component, the tester includes a temperature sensor placed in contact with the optical component and a reference temperature sensor placed in the vicinity of the optical component.

24 Claims, 4 Drawing Sheets

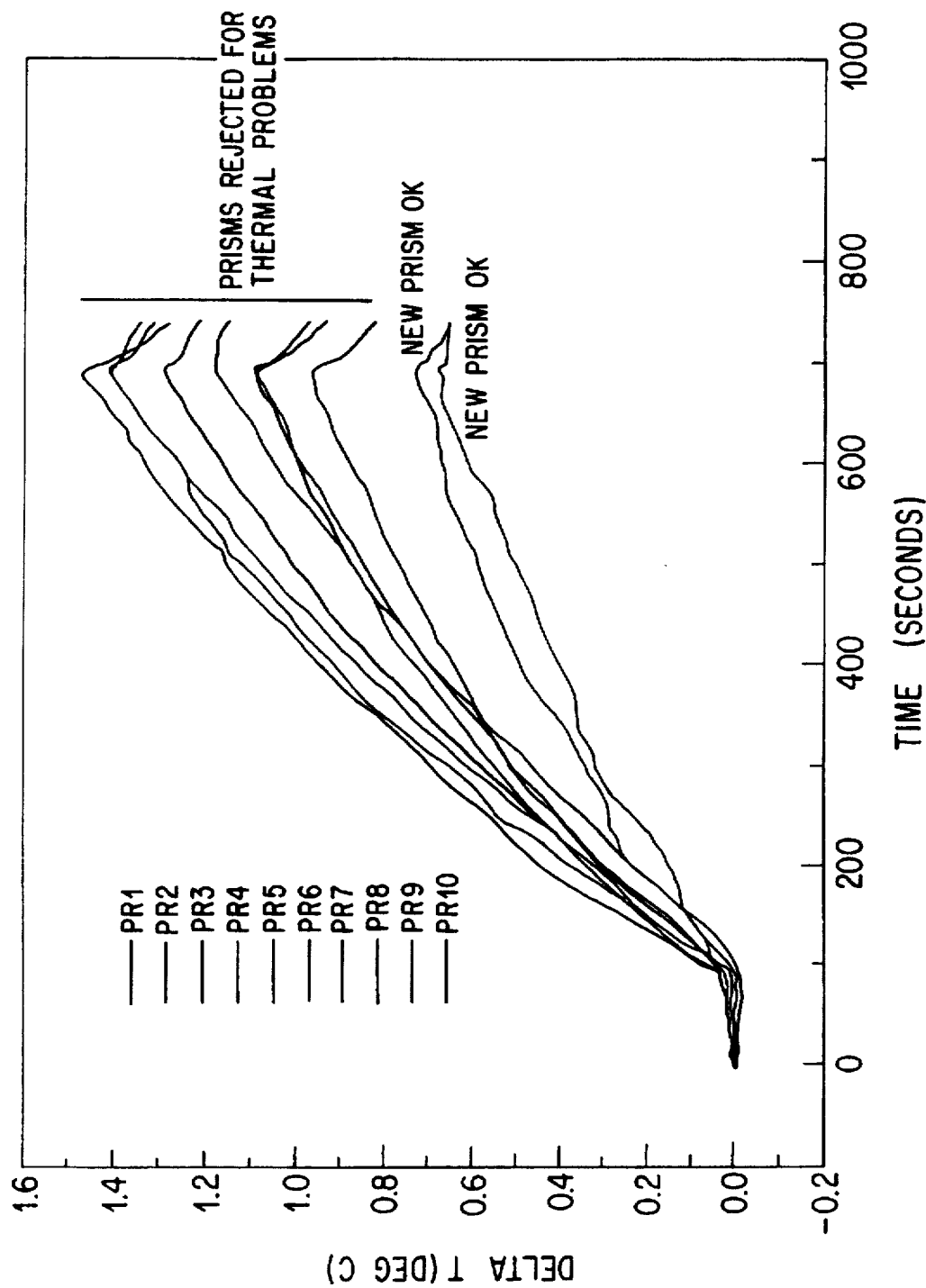

1

ABSORPTION TESTER FOR OPTICAL COMPONENTS

FIELD OF THE INVENTION

This invention relates to optical components and, in particular, to a technique for detecting the optical absorption by light-transmitting optical components.

BACKGROUND

Light-transmitting optical components, such as prisms, windows, and lenses, are frequently used in optical systems for a laser or other light source. The effect of a light-transmitting optical component on the emergent wavefront represents an important specification for the optical component. Light absorption by the optical component develops internal thermal gradients which are manifested as wavefront distortions. A wavefront distortion is the total, peak-to-peak, deformation in the direction of propagation of the emergent wavefront from its intended shape. Wavefront distortions can cause spherical lensing or other distortions that degrade the overall performance of the optical system.

Accordingly, it is generally desirable to measure the light absorption of optical components to assess their performance prior to being incorporated in an optical system. Measuring optical absorption indirectly by using optical detectors such as photodiodes or photomultipliers represents one well known method of measuring the absorption of optical components. In particular, this method involves comparing the difference between the intensity of a light beam entering an optical component and the intensity of the light beam exiting the optical component (and accounting for reflection losses which also must be measured) to calculate the absorption of the optical component.

Unfortunately, measurements performed by the above-described method become increasingly difficult as the absolute value of the absorption of the optical component decreases. For example, absorptions may be on the order of 1% or less of the incident light. The above-described method is especially difficult when differences on the order of a fraction of a percent are important, because drift and noise in the optical source and the optical detectors limit the accuracy of the absorption measurements. Further, this method requires deducing the absorption by measuring the difference between two potentially very large numbers (i.e., the intensity of a light beam entering the optical component and the intensity of the light beam exiting the optical component). Moreover, this method requires several expensive optical sensors which must be placed in a spread-out arrangement for each optical component to be tested.

What is needed is a better structure and technique for measuring optical absorption so that light-transmitting optical components are selected efficiently and accurately for use in a particular optical system.

SUMMARY

The present invention provides a technique for detecting the light absorption of optical components by measuring the increase in temperature of the optical component that results from light absorption. One embodiment provides a multiple optical component absorption tester that includes a temperature sensor placed in contact with each optical component and a reference temperature sensor placed in the vicinity of each optical component to compensate for changes in ambient temperature that occur during the testing of the multiple optical components. This embodiment provides a less expensive and more compact absorption tester for simultaneous testing of multiple optical components.

Determining light absorption using the invention is very accurate because, rather than measuring the difference in quantity of two large numbers (i.e., the intensity of a light beam entering the optical component and the intensity of the light beam exiting the optical component), the inventive technique measures the temperature increase of the optical component, which is directly related to the amount of energy absorbed by the optical component. The invention is particularly advantageous for selecting light-transmitting optical components for use in applications in which small differences in optical absorption produce large differences in performance, such as in ultraviolet (UV) excimer lasers.

BRIEF DESCRIPTION OF THE DRAWINGS

FIG. 4 is a graph of light absorption of optical components tested in accordance with one embodiment of the invention.

DETAILED DESCRIPTION OF THE PREFERRED EMBODIMENTS

All materials absorb radiation in some parts of the electromagnetic spectrum. The amount of absorption depends on the wavelength of the radiation, the amount of absorbing material in the path of the radiation, and the absorptance of the material at that wavelength. Optical components, such as light-transmitting optical components used in a laser, that absorb light develop internal thermal gradients that cause wavefront distortions. The preferred embodiment of the invention determines absorption of an optical component by measuring the temperature increase of the optical component that directly results from the optical absorption.

Figure 1:
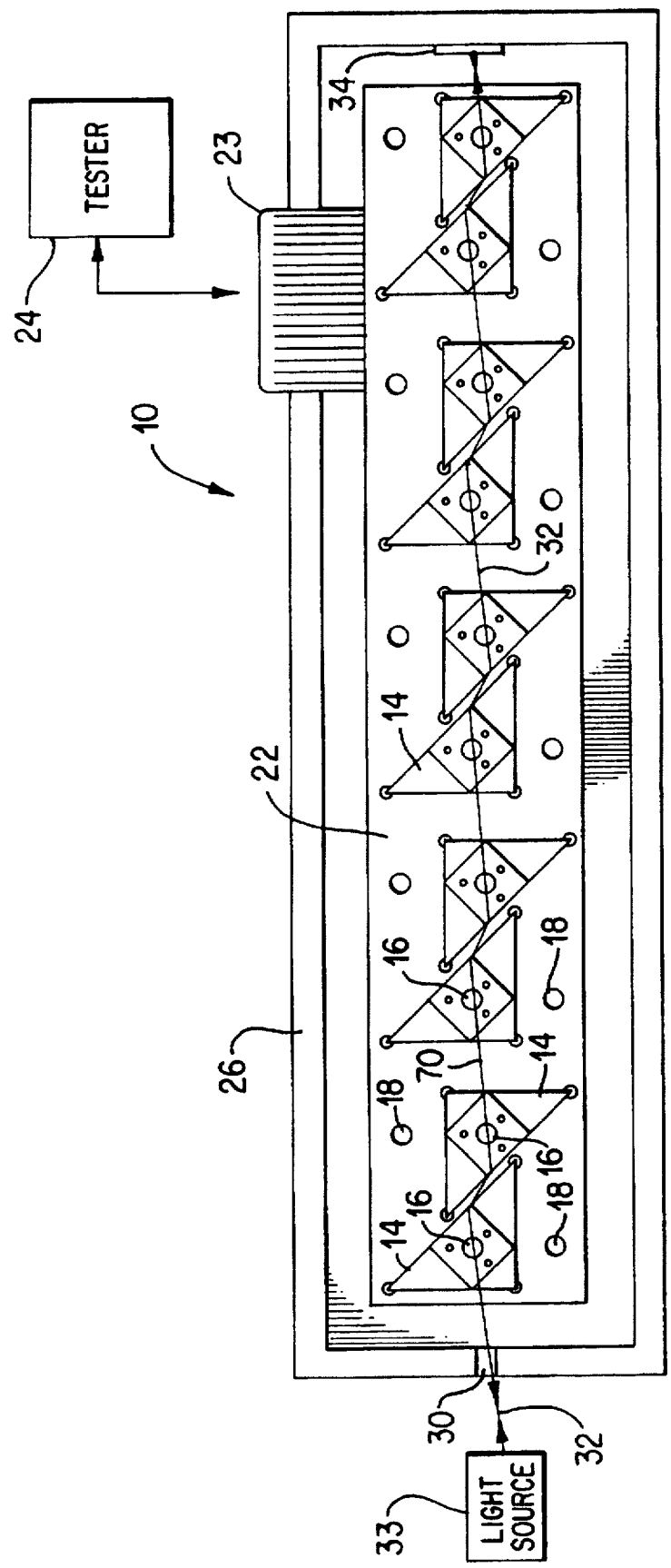
FIG. 1 is a top down view of an optical absorption tester, with its cover removed and certain portions made transparent, for multiple prisms in accordance with one embodiment of the invention.

FIG. 1 illustrates an optical absorption tester 10 configured for testing multiple prisms in accordance with one embodiment of the invention, although any single optical component or any multiple optical components may instead be tested. An example will be given of absorption tester 10 measuring the optical absorption of fused silica prisms 14 for use in a krypton fluoride (KrF) excimer laser operating at a wavelength of 248 nm. As shown in FIG. 1, tester 10 holds up to ten fused silica prisms 14 for testing them simultaneously. Thus, tester 10 advantageously reduces the time required to test the optical absorption of multiple prisms or other optical components.

A temperature sensor 16 is placed in contact with each prism 14. Tester 10, in the particular example, includes ten temperature sensors 16, one for each prism 14 to be tested. In one embodiment, the temperature sensors are resistance temperature detector (RTD) type sensors.

Such temperature sensors reflect temperature by the change in resistance of a resistive element having a known thermal coefficient of resistance. This change in resistance is converted into a voltage using conventional techniques. Any temperature sensor may be used instead of an RTD type.

Tester 10 also includes a reference temperature sensor 18 (identical to sensor 16) placed in the vicinity of each prism 14. Tester 10 includes ten reference temperature sensors 18, one for each prism 14 to be tested. The reference temperature sensors 18 measure local variations in ambient temperature in the vicinity of the prisms. The signals generated by the reference temperature sensors 18 are subtracted from the signals generated by sensors 16 so that the signal derived by each sensor 16 solely results from the change in temperature of the prism 14.

Figure 3:
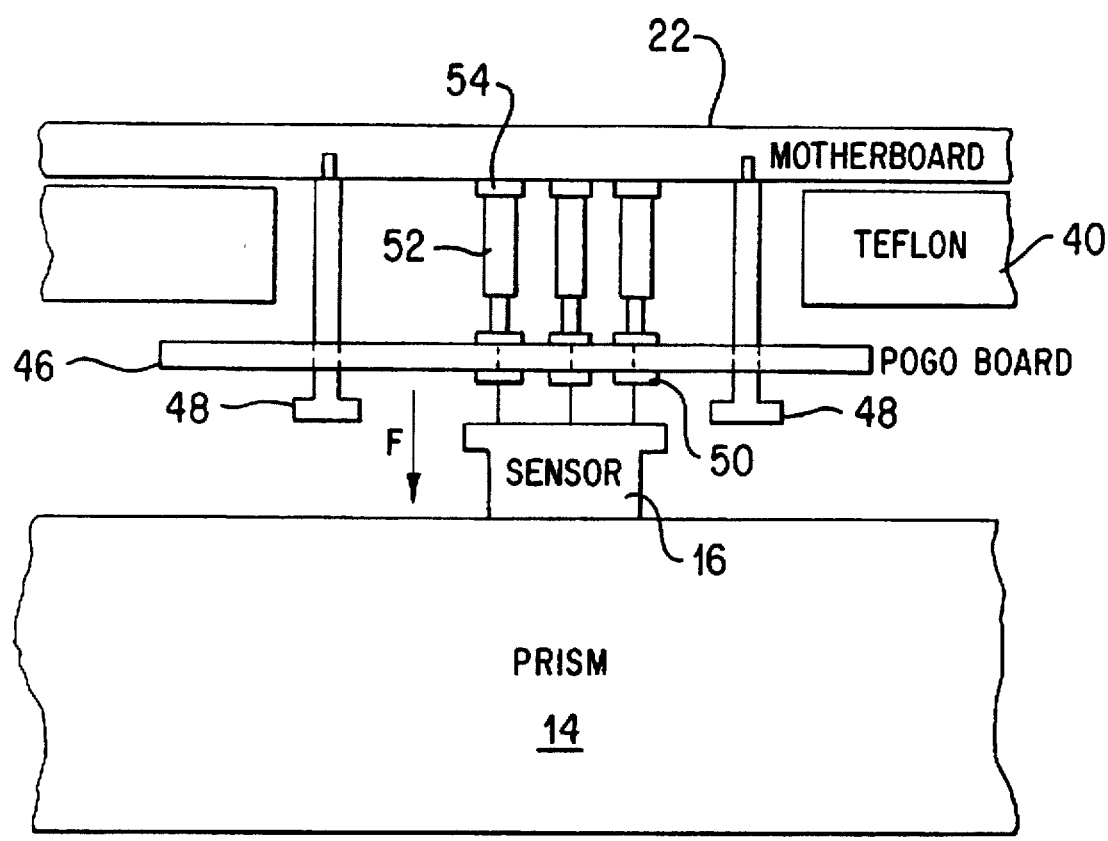
FIG. 3 is a partial cross-section of the tester of FIG. 1 showing details of the mounting of the temperature sensor to the motherboard.

Tester 10 includes a motherboard 22 for supporting sensors 16 and 18, to be described in greater detail with respect to FIG. 3. The motherboard 22 also provides an electrical connector 23 having conductors leading to sensors 16 and 18. A suitable testing apparatus 24 is connected to connector 23 to provide any supply voltage to the sensors and to measure the sensor signals.

Figure 2:
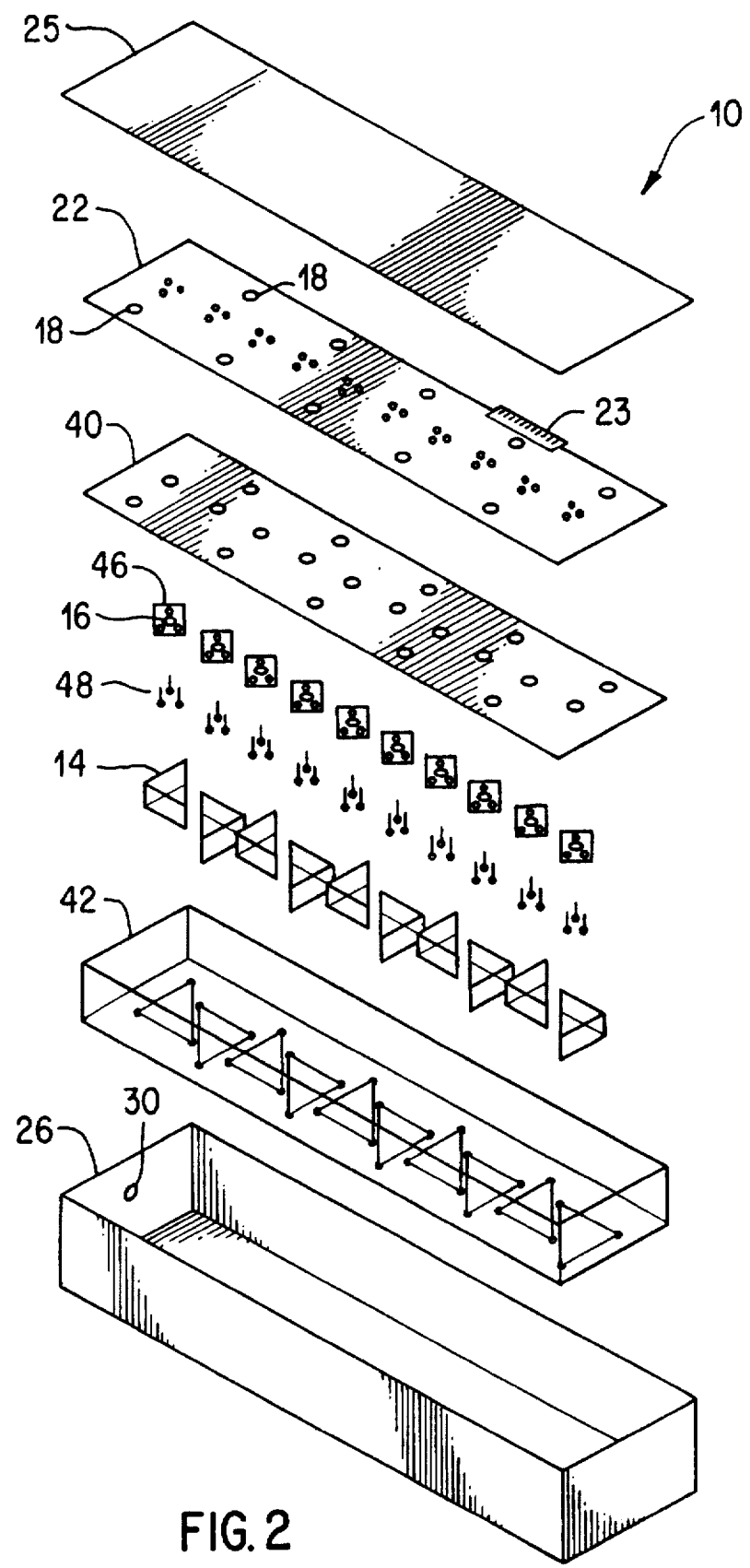
FIG. 2 is an exploded view of the optical absorption tester of FIG. 1.

The motherboard 22 is enclosed in a housing that includes an aluminum cover 25 (FIG. 2) and an aluminum base 26 (FIG. 2). The housing reduces the cooling effects of convection currents present in the room in which the testing is being performed.

An aperture 30 (FIG. 1) is provided in the base 26 to allow a light beam 32 from a light source 33 to enter and exit the housing. A mirror 34 is also provided to double pass light beam 32 to thereby improve the sensitivity of tester 10 for testing low levels of optical absorption and to make the incident power on all of the prisms 14 approximately equal.

The operation of the optical absorption tester 10 is discussed in detail below. Optical absorption testing using tester 10 is performed by passing a light beam 32 from a light beam source 33, such as a laser, through each prism 14. In one embodiment, the light beam source is a KrF excimer laser operating at 248 nm. The absorption of light beam 32 either internal to a prism 14 or at the surface of a prism 14 causes the temperature of the prism 14 to increase. The preferred technique allows measurement of the sum of both surface and bulk related absorption without having to measure surface reflection.

Tester 10 uses temperature sensors 16 to measure the temperature increase of each prism 14 during testing. In the preferred embodiment, each sensor 16 directly contacts a respective prism 14. Tester 10 uses reference temperature sensors 18 to account for local variations in ambient temperatures in the vicinity of each prism 14 during testing. The magnitude of the temperature increase of a prism 14 is directly proportional to the total absorption by the prism.

Small variations in the intensity of light beam 32 are not critical in this temperature measuring technique. It is possible to simultaneously test a plurality of prisms 14 in series without seriously depleting the power in light beam 32 along the light path, because the optical absorption of each prism 14 is relatively small. For example, optical absorption testing according to the preferred technique was performed on a fused silica prism. A light beam generated by a UV excimer laser was passed through the prism for about ten minutes causing a 2.9° C. increase in temperature of the prism, measured by a temperature sensor contacting the prism. An increase in temperature of 2.9° C. of the prism, which is easily measured, requires approximately 157 joules. The prism was exposed to a total dose of approximately 12,000 joules during the ten minutes of testing. Assuming no surface absorption, a reflectance loss of approximately 0.1% per surface changes the amount of power absorbed by the prism by a negligible amount. Thus, the optical absorption of the prism is approximately 157 joules divided by 12,000 joules, which equals 1.313% of the energy applied to the prism.

As seen, a relatively small absorption of the prism, in the vicinity of 1% of incident light, is converted into a relatively large temperature rise of several degrees centigrade. The tester 10, as configured, can measure temperature rises as small 0.05° C., ensuring a very accurate detection of the absorption of the prism.

Detecting the temperature of an optical component may be performed in various ways, which may be electrically, mechanically, optically, or chemically. In one embodiment, the temperature sensors are thermocouple sensors. Any techniques of measuring the temperature of optical components in response to a light beam may be used by the optical absorption tester 10 of FIG. 1.

Although a specific structure is shown for optical absorption testing of particular optical components (i.e., prisms), other suitable embodiments may be employed for optical components of different geometries such as windows, mirrors, or lenses.

FIG. 2 is an exploded view of the optical absorption tester 10 of FIG. 1. Elements in FIGS. 1 and 2 which are identical are labeled with the same numeral. As shown in FIG. 2, tester 10 includes an aluminum base 26 and an aluminum cover 25 which provide the housing to enclose the prisms 14 during testing by tester 10.

Tester 10 also includes a teflon spacer 40 and a teflon sink 42 (shown partially transparent) for mounting prisms 14 and for thermally isolating prisms 14 so that the maximum temperature increase can be produced by light beam 32 (FIG. 1). This increases the ability of tester 10 to measure very low levels of optical absorption. Pogo boards 46 and shoulder screws 48 are used for supporting sensors 16 against the prisms to be tested, shown in greater detail in FIG. 3.

FIG. 3 is a cross-sectional view across one of the pogo boards 46. Temperature sensor 16 is shown having three leads connected to corresponding contact pads 50 on pogo board 46. The contact pads 50 are electrically connected to pogo pins 52, which are spring-loaded and compressible (like a pogo stick). Shoulder screws 48 slideably extend through pogo board 46 and are screwed into the motherboard 22. Pogo pins 52 thus urge pogo board 46 away from the motherboard 22. Pogo pins 52 make electrical contact with pads 54 on the motherboard 22, which are connected via conductive traces to the electrical connector 23 (FIG. 2). The motherboard 22 is then placed over the prisms 14 such that sensors 16 contact the prisms 16. The pogo pins 52 provide a spring force F to ensure a reliable direct contact between sensors 16 and prisms 14.

The teflon spacer 40 is shown positioned between the motherboard 22 and prisms 16 to provide thermal insulation of prisms 16.

FIG. 4 is a graph of the temperature rise due to optical absorption of fused silica prisms measured using the technique of the preferred embodiment. In particular, FIG. 4 shows the change in temperature vs. time for ten prisms tested with the optical absorption tester 10 of FIG. 1. FIG. 4 also shows that the eight prisms which had the greatest temperature rise did not meet the tester's criteria for acceptability and that the remaining two prisms were acceptable. The prisms which were rejected were likely to cause problems if installed in a laser application, such as a stepper. It is far more economical, convenient, and expedient to use the present invention to reject unsuitable prisms prior to those prisms being installed in an application than to discover the unsuitability of those prisms in an expensive full laser system test.

While particular embodiments of the present invention have been shown and described, it will be obvious to those skilled in the art that changes and modifications may be made without departing from this invention in its broader aspects. For example, tester 10 in FIG. 1 may be reduced in size and used to determine the optical absorption of one optical component at a time. Therefore, the appended claims are to encompass within their scope all such changes and modifications as fall within the true spirit and scope of this invention.

What is claimed is:

1. A method for measuring optical absorption comprising providing multiple light-transmitting optical components;

passing at least a portion of a light beam through said multiple light-transmitting optical components in series; and measuring an increase in temperature of each of said multiple light-transmitting optical components caused by said light beam being absorbed by each of said multiple light-transmitting optical components to determine light absorption of each of said multiple light-transmitting optical components.

2. The method of claim 1 further comprising energizing a laser, wherein said light beam is generated by said laser, said laser generating light of approximately the same wavelength as a laser system in which at least one optical component is intended to be used.

3. The method of claim 1 wherein said step of measuring comprises measuring an increase in temperature of each of said multiple light-transmitting optical components using at least one temperature sensor.

4. The method of claim 3 wherein said temperature sensor is a resistive temperature sensor.

5. The method of claim 1 wherein said step of measuring comprises:

measuring any variations in ambient temperature in the vicinity of each of said multiple light-transmitting optical components using a reference temperature sensor.

6. The method of claim 1 wherein said step of measuring comprises:

simultaneously measuring increases in temperature of said multiple light-transmitting optical components caused by the light beam passing through said multiple light-transmitting optical components, wherein the increases in temperature are related to light absorption of said multiple light-transmitting optical components.

7. The method of claim 1 further comprising:

double passing at least a portion of the light beam through said multiple light-transmitting optical components.

8. The method of claim 1 further comprising:

determining a quality of each of said multiple light-transtmitting optical components based on said increase in temperature.

9. An optical absorption testing system comprising:

a support structure that supports multiple light-transmitting optical components;

a mirror for double passing at least a portion of a light beam through said multiple light-transmitting optical components supported by said support structure; and at least one temperature sensor in contact with each of said multiple light-transmitting optical components to be tested by the optical absorption testing system.

10. The system of claim 9 further comprising:

at least one reference temperature sensor placed in the vicinity of said multiple light-transmitting optical components to be tested by the optical absorption testing system.

11. The system of claim 9 further comprising:

a housing that encloses said support structure during testing.

12. The system of claim 9 further comprising a laser, said laser producing a laser beam applied to each of said multiple light-transmitting optical components.

13. An apparatus for simultaneous measuring of optical absorption of multiple light-transmitting optical components comprising:

a support structure that supports multiple light-transmitting optical components;

multiple temperature sensors, each of said temperature sensors being placed in contact with at least one of said optical components;

multiple reference temperature sensors, each of said reference temperature sensors being placed in the vicinity of at least one of said optical components; and a housing enclosing said optical components during the simultaneous measuring of optical absorption of said optical components.

14. The apparatus of claim 13 further comprising:

a mirror that double passes at least a portion of a light beam through each of said optical components.

15. The apparatus of claim 13 further comprising:

means for thermally isolating said optical components.

16. The apparatus of claim 14 wherein the number of said multiple temperature sensors equals the number of said optical components.

17. A method for measuring optical absorption comprising:

providing multiple light-transmitting optical components;

providing light to said multiple light-transmitting optical components; and measuring an increase in temperature of each of said multiple light-transmitting optical components caused by said light being absorbed by each of said multiple light-transmitting optical components to determine light absorption of each of said multiple light-transmitting optical components;

wherein said step of providing light comprises:

passing at least a portion of a light beam through said multiple light-transmitting optical components in series.

18. The method of claim 17 further comprising energizing a laser, wherein said light is generated by said laser, said laser generating light of approximately the same wavelength as a laser system in which at least one optical component is intended to be used.

19. The method of claim 17 wherein said step of measuring comprises measuring an increase in temperature of each of said multiple light-transmitting optical components using at least one temperature sensor.

20. The method of claim 19 wherein said temperature sensor is a resistive temperature sensor.

21. The method of claim 17 wherein said step of measuring comprises:

measuring any variations in ambient temperature in the vicinity of each of said multiple light-transmitting optical components using a reference temperature sensor.

22. The method of claim 17 wherein said step of measuring comprises:

simultaneously measuring increases in temperature of said multiple light-transmitting optical components caused by the light beam passing through said multiple light-transmitting optical components, wherein the increases in temperature are related to light absorption of said multiple light-transmitting optical components.

23. The method of claim 17 further comprising:

double passing at least a portion of the light beam through said multiple light-transmitting optical components.

24. The method of claim 17 further comprising:

determining a quality of each of said multiple light-transmitting optical components based on said increase in temperature.

* * * * *